United States Patent [19]

Eberhard et al.

[11] Patent Number: 5,712,926
[45] Date of Patent: Jan. 27, 1998

[54] X-RAY COMPUTED TOMOGRAPHY (CT) SYSTEM FOR DETECTING THIN OBJECTS

[76] Inventors: Jeffrey Wayne Eberhard, 5 Tokay La.; Meng-Ling Hsiao, 2191 Foxhill Dr., both of Niskayuna, N.Y. 12309

[21] Appl. No.: 325,145

[22] Filed: Oct. 20, 1994

[51] Int. Cl.$^6$ ............................................. G06K 9/46
[52] U.S. Cl. ............................................. 382/205; 378/57
[58] Field of Search ............................................. 382/100, 131, 382/154; 378/4, 20, 57, 62; 250/390.01, 390.04, 390.06

[56] References Cited

U.S. PATENT DOCUMENTS

| | | | |
|---|---|---|---|
| 4,791,567 | 12/1988 | Cline et al. | 382/131 |
| 4,903,202 | 2/1990 | Crawford | 382/131 |
| 4,905,148 | 2/1990 | Crawford | 382/131 |
| 5,022,062 | 6/1991 | Annis | 382/100 |
| 5,044,002 | 8/1991 | Stein | 378/57 |
| 5,479,023 | 12/1995 | Bartle | 378/57 |

OTHER PUBLICATIONS

Copley et al., "Computed Tomography Part I: Introduction and Industrial Applications," *The Journal of The Minerals, Metals & Materials Society*, vol. 486, No. 1, Jan. 1994, pp. 14–26.

Horn, *Robot Vision*, Chapter 4, MIT Press 1986, pp. 65–71.

*Primary Examiner*—Joseph Mancuso
*Assistant Examiner*—Gerard Del Rosso
*Attorney, Agent, or Firm*—Foley & Lardner

[57] ABSTRACT

A technique to ascertain the presence or absence of an object in a three-dimensional volume, such as explosives in the side walls of luggage. The technique involves radiation scanning the three-dimensional volume to determine a property of each of a plurality of voxels representing the three-dimensional volume and to identify voxels having similar values of the property to identify a contiguous group of voxels having the similar values. Then, the contiguous group of voxels is identified as containing the object if a characteristic (such as mass and/or volume) of the contiguous group has a predetermined value.

6 Claims, 5 Drawing Sheets

FIG. 1

100% EXPLOSIVE
$\rho$ = 1.5 gm/cc

FIG. 2

20% EXPLOSIVE
$\rho$ = 0.3 gm/cc

X-RAY COMPUTED TOMOGRAPHY (CT) SYSTEM FOR DETECTING THIN OBJECTS

BACKGROUND OF THE INVENTION

The invention is directed to an improved technique for the detection of thin objects, for example, explosives along the walls of luggage. More specifically, the invention is directed to an improved technique for the detection of thin objects such as explosives using X-ray computed tomography (CT).

Detection of explosives in luggage is an extremely challenging problem because the amount of explosive required to do catastrophic damage is relatively small and because plastic explosives can be formed into almost any desired shape. Perhaps the most challenging configuration for detection is sheet explosive, where the material is deformed into a thin sheet with a very small physical extent in one direction.

One conventional way of detecting explosives is through the use of X-ray CT. X-ray CT is a technique which determines the internal make-up of an object by passing X-rays through the object and measuring the attenuation of the X-rays passing through the object. In this technique the object is sub-divided into many voxels, a voxel being the basic volumetric unit for imaging purposes. Compared with other objects in luggage, explosives have a specific range of densities, for example, 1.2 to 1.8 gm/cc, and accordingly attenuate X-rays differently than non-explosives.

In general, CT systems are designed so that the voxel size roughly corresponds to the smallest object of interest in the image. In cases where high contrast sensitivity is required, this approach is clearly justified. Indeed, voxel sizes somewhat smaller than the spatial dimension of interest are often used. However, this approach greatly increases system cost and complexity because it requires a large number of detector elements, view angle positions, and voxels for image acquisition and reconstruction. X-ray source loading is also significantly increased due to the need to maintain roughly the same number of X-rays and hence the same signal-to-noise ratio for the smaller voxel dimensions.

Figure 1:
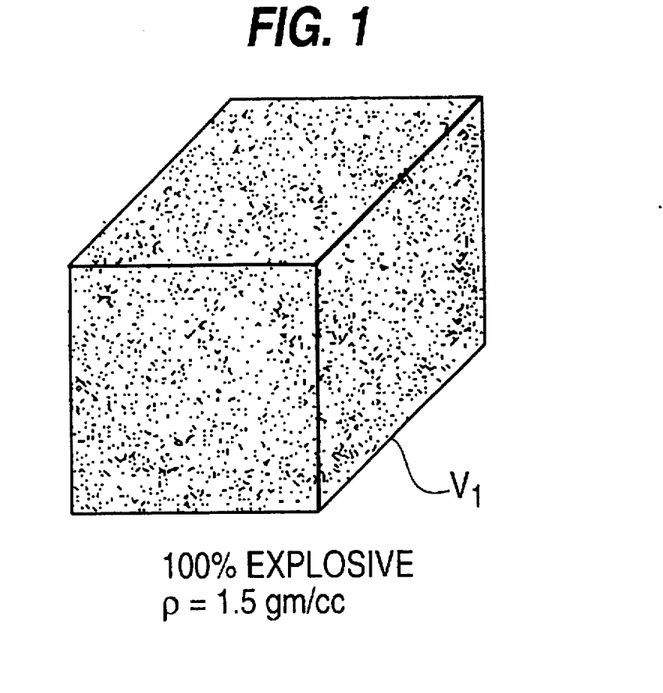
FIG. 1 illustrates a completely filled-in voxel $V_1$ having an average density $\rho$ of 1.5 gm/cc.
Figure 2:
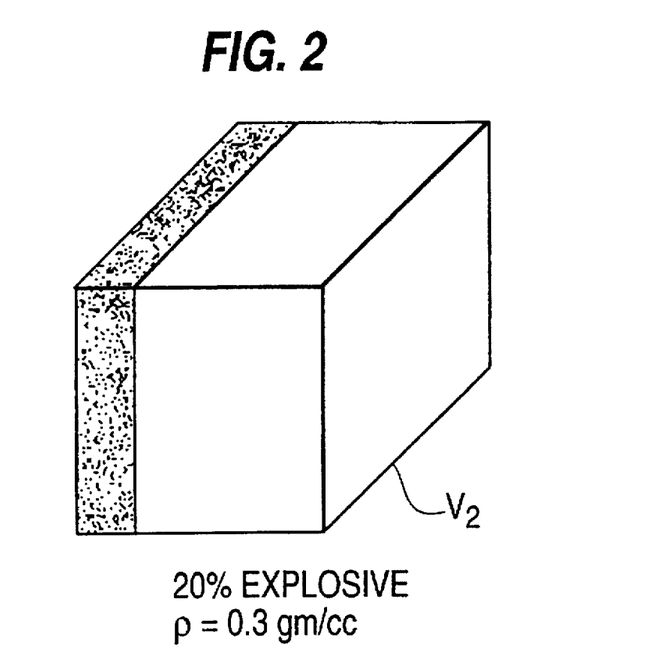
FIG. 2 illustrates a partially filled-in voxel $V_2$ having an average density $\rho$ of 0.3 gm/cc.

If the thin dimension of the sheet of explosive is smaller than the linear voxel dimension in a CT image, the measured density of a voxel of interest decreases due to the fact that the voxel is not completely filled with explosive. FIGS. 1 and 2 illustrate this problem for a configuration with an explosive density $\rho$ of 1.5 gm/cc. FIG. 1 shows a voxel $V_1$ completely filled with explosive, wherein the average density of the voxel is 1.5 gm/cc. FIG. 2 shows a voxel $V_2$ containing a section of sheet explosive, where the thickness of the sheet is 20% of the voxel linear dimension. The average density $\rho$ in the voxel $V_2$ is reduced to 0.3 gm/cc. Conventional CT systems would compute a density for voxel $V_2$ which is less than the density expected for an explosive and thus would not identify voxel $V_2$ as containing an explosive.

The challenge is to discriminate such a sheet explosive from background material in the suitcase.

SUMMARY OF THE INVENTION

An object of the invention, therefore, is to determine the presence or absence of an object in a three-dimensional space when the object is thin in one dimension.

Another object of the invention is to provide an improved technique for detecting explosives.

Another object of the invention is to provide a technique for detecting explosives which minimizes the number of voxels required to be processed while at the same time providing for the detection of sheet explosives, for example, along the walls of luggage.

Yet another object of the invention is to provide a low cost X-ray computed tomography system for explosives detection.

A technique according to the invention ascertains the presence or absence of an object in a three-dimensional volume, such as explosives in luggage. The technique according to the invention employs radiation scanning of the three-dimensional volume to determine a property (for example, density) of each of a plurality of voxels representing the three-dimensional volume and identifying voxels having similar values of the property to identify a contiguous group of voxels having the similar values. Then, the contiguous group of voxels is identified as containing the object if a characteristic of the contiguous group has a predetermined value.

Other objects, features, and advantages of the invention will become apparent from the detailed description of the invention set forth below.

BRIEF DESCRIPTION OF THE DRAWINGS

The invention will be described in greater detail below with reference to the accompanying drawings, wherein.

DETAILED DESCRIPTION OF THE PREFERRED EMBODIMENTS

The invention relies on the fact that explosives have a specific range of densities as compared to other items such as clothing in luggage and on the fact that many explosives must be physically in one piece, that is, contiguous, in order to detonate properly. According to the invention, an image processor performs connected component identification and labeling to identify regions of a specific range of densities and connects them into a single volume. The size of the single volume is then calculated to determine if the single volume is large enough to cause significant damage if the single volume contained explosives.

Because the present invention is cheaper than a conventional CT system it can be used, for example, for initial screening. A secondary inspection, for example, by neutron or manual inspection, can be used to confirm that the suspect region is really an explosive.

In this new technique according to the invention, a priori knowledge is combined with image processing and analysis to provide a system configuration with a larger voxel size. Consider, for example, a sheet of explosive 2 mm thick with a density of 1.5 gm/cc. In a conventional CT system, a voxel size of 2 mm would be required and 500 detector elements would be required to cover a 1 m field of view. Approximately 1000 view angles would be needed to reconstruct the 500×500 image necessary to maintain system spatial resolution. Such a system is extremely complex and expensive in comparison with the present invention, which allows use of a larger voxel size.

Figure 3:
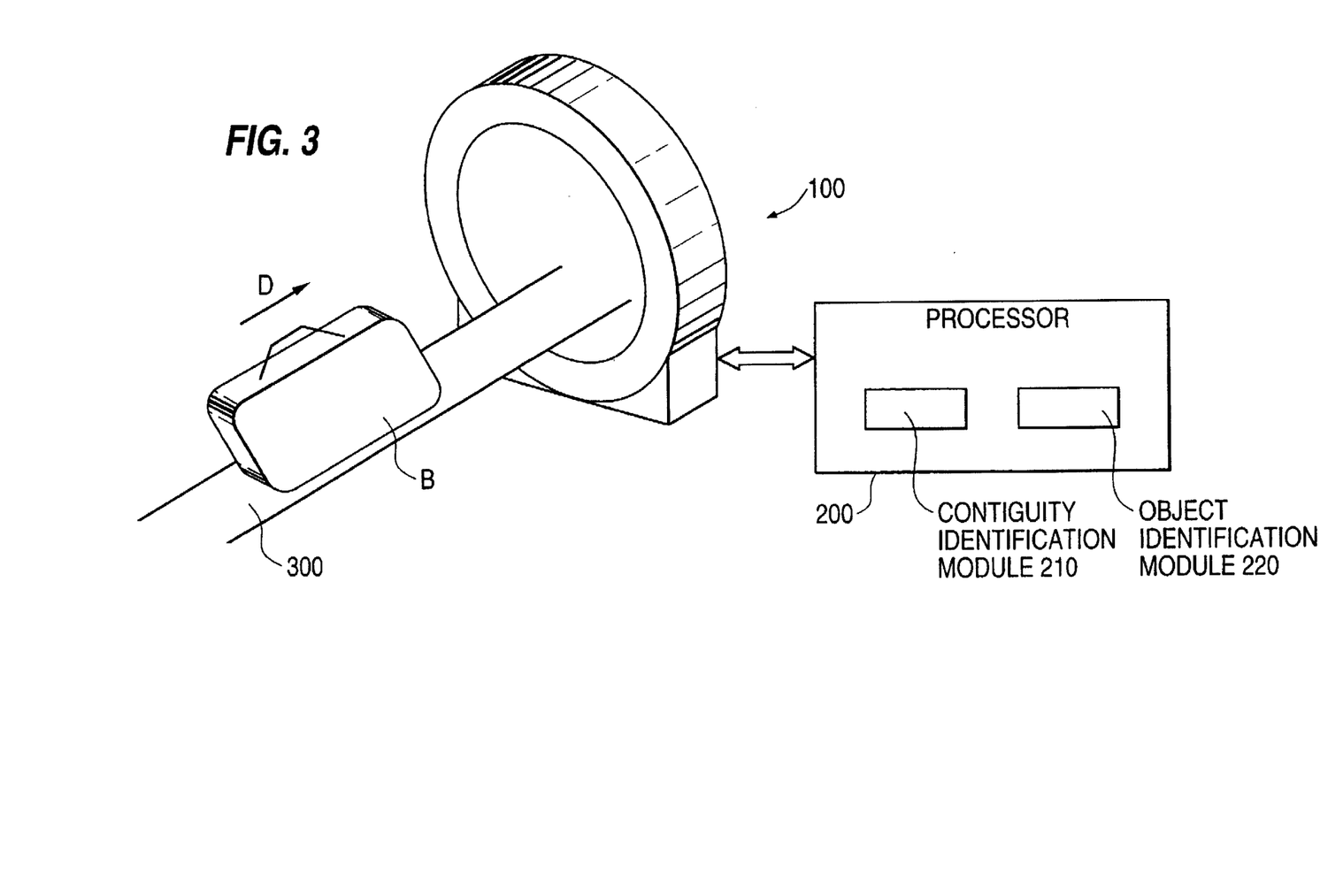
FIG. 3 is a perspective view of a suitable hardware arrangement according to the invention.
Figure 4:
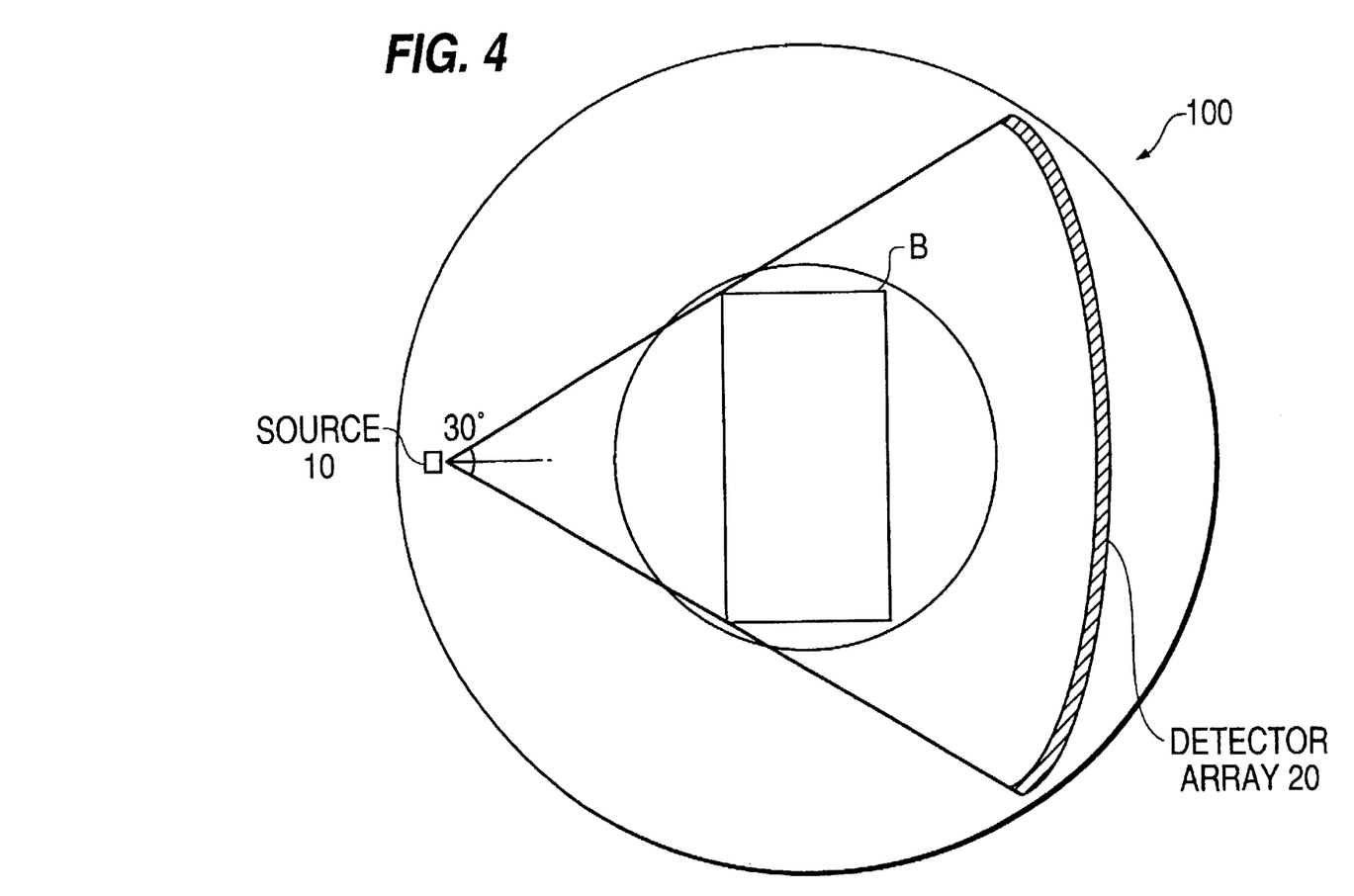
FIG. 4 is an end view of a gantry suitable for use in the invention.

FIGS. 3 and 4 illustrate hardware suitable for use in a preferred embodiment of the invention. FIG. 3 is a perspective view which shows a bag B which is to be inspected. The bag B is moved along a conveyor 300 in direction D toward a gantry 100. The gantry 100 contains an X-ray source which emits X-rays into the bag as the bag passes through the gantry 100. The gantry 100 also includes a set of X-ray detectors. The detectors detect X-rays which passed through the bag B. Information from the detectors is sent to a processor 200 to determine the attenuation of the X-rays as they pass through the bag. The processor 200 includes a contiguity identification module 210 and an object identification module 220, both of which will be described in further detail below. The attenuation information is used by processor 200 to compute a density for each voxel in a three-dimensional image of the bag.

Reconstruction of a three-dimensional density map of the bag requires that the bag be viewed at various angles. Accordingly, either the gantry 100 must be rotated around the bag or the bag must be rotated. In the arrangement shown in FIGS. 3 and 4, the gantry 100 is rotated because the contents of the bag would shift if the bag were rotated.

FIG. 4 shows an end view of gantry 100. In the FIG. 4 implementation of the invention, gantry 100 is sized to accommodate a maximum bag size of 100 cm×50 cm. The gantry 100 includes an X-ray source 10 and a detector array 20. The source 10 is a 140 kVp, 1 to 5 kW source and has a 30° fan angle. The detector array 20 has 1280 detection elements in an 8×160 array. Each detector element consists of a scintillator coupled to a photodiode and associated current integration electronics. The voxel size in this embodiment is 0.625×0.625×1.25 cm. The number of slices for a typical bag (75 cm×50 cm×20 cm) is 60. The total inspection time for a typical bag is 8 seconds based on 250 views.

General background on CT scanning, hardware, and signal processing may be found in "Computed Tomography Part I: Introduction and Industrial Applications," *The Journal of The Minerals, Metals & Materials Society*, David C. Copley, Jeffrey W. Eberhard, and Gregory A. Mohr, Vol. 46, No. 1, January 1994, pp. 14–26; *Principles of Computerized Tomographic Imaging*, Avinash C. Kak and Malcolm Slaney (IEEE Press 1988); and *Image Reconstruction From projections*, Gabor T. Herman (Academic Press 1980). The entire contents of these publications are incorporated herein by reference.

Figure 5:
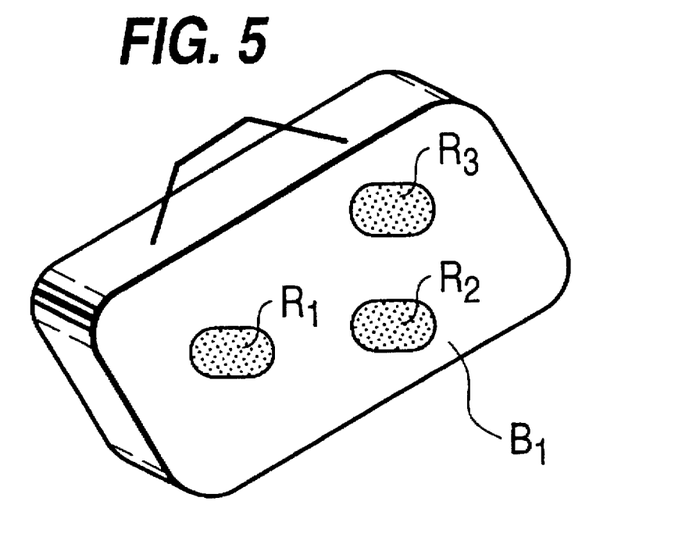
FIG. 5 illustrates a harmless bag $B_1$ with small regions of a specific range of densities not connected together.
Figure 6:
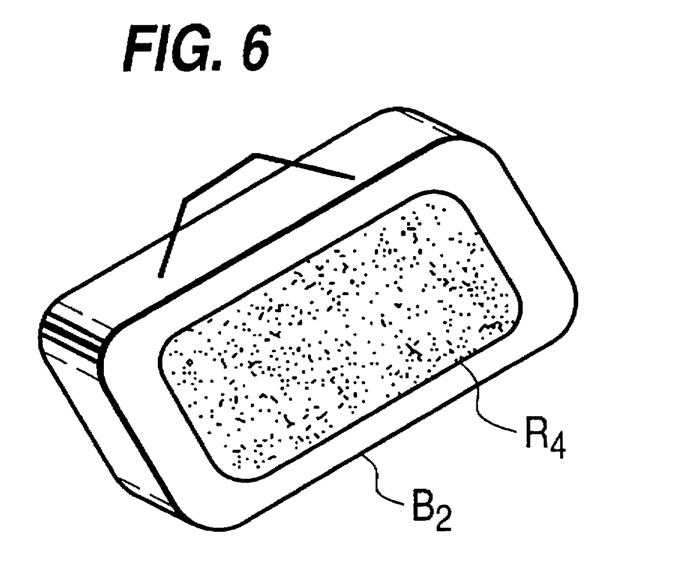
FIG. 6 illustrates a suspicious bag $B_2$ with a large contiguous region having a specific range of densities.

In this new technique according to the invention, a large voxel size on the order of 1 cm can be employed. A large sheet of explosive passing through a given voxel would fill 20% of the voxel volume, resulting in an average density of the voxel of 0.3 gm/cc. This density is still sufficiently large to be discriminated against a background bag density of 0.2 gm/cc. Thus, voxels within a chosen range of densities, for example, from 0.25 to 1.8 gm/cc are identified as potentially containing explosives. These regions which have densities within a specific range are illustrated in FIGS. 5 and 6 as regions $R_1$, $R_2$, $R_3$, and $R_4$. FIGS. 5 and 6 will be discussed in more detail below.

After the above-background regions are identified, a three-dimensional grey-scale connected component identification and labeling process joins all physically adjacent voxels in the selected density range. Component identification and labeling techniques are set forth in Chapter 4 of *Robot Vision* by Berthold Klaus Paul Horn (MIT Press 1986). This publication is incorporated herein by reference.

The procedures described in this text are modified for use in the present invention in that the present invention employs a three-dimensional grey scale procedure instead of a two-dimensional binary procedure. Instead of checking to determine if a voxel is a 1, a check is made to determine if its difference $\Delta$ with respect to a selected reference value is less than a preset threshold. If it is, the voxel is treated just like a 1 in the binary case. In three-dimensions, volumes are used instead of areas. For any given voxel, the neighbors are divided into a plane above, a same plane, and a plane below the voxel of interest. A three-dimensional raster scan is performed, proceeding from top to bottom, while a scan within a plane is a two-dimensional raster scan. As in the two-dimensional case, a subset of the neighboring elements is used in the labeling scheme. All voxels in the plane above are evaluated. If any voxel in the plane above is within the threshold difference value $\Delta$ of the target voxel, it is assigned the label of that voxel. In the plane of the voxel of interest, the same voxels as in the two-dimensional case are utilized. As in the two-dimensional case, it is possible that two different labels have been used for parts of one component. Indeed, this is the case if the two voxels which give labels to the central voxel of interest are connected only point-wise to the central voxel (not on a face or edge). In such a case, it is necessary to note that the two labels are equivalent and use either of them for the central voxel. Re-labeling using a second scan over the image may be necessary.

Voxels in the specified density range which are physically adjacent in three-dimensions and have a density variation less than a predetermined threshold are grouped and assigned with a label for identification. Because this adjacency check is performed in three-dimensions, thin regions of any shape in any orientation are easily identified.

Next, the number of voxels in each region is determined and compared to a threshold. Small regions, that is, regions containing only a small number of voxels are rejected as being "harmless." This situation is illustrated in FIG. 5, which shows a "harmless" bag $B_1$ with small regions $R_1$, $R_2$, and $R_3$ in the specified density range not connected together. Large contiguous regions, that is, regions containing more voxels than a preset threshold, are identified as suspect. This situation is illustrated in FIG. 6, which shows a suspicious bag $B_2$ with a large contiguous region $R_4$ of material in the specified density range. The mass contained in any suspect region(s) is then calculated by multiplying the volume of each voxel in the region by its density. If the resulting mass is greater than a preset threshold, for example, 1000 gm, the region is tentatively identified as explosive. Verification may then be performed, either by a second inspection technique, such as pulsed fast neutron analysis or by opening the bag.

Figure 7:
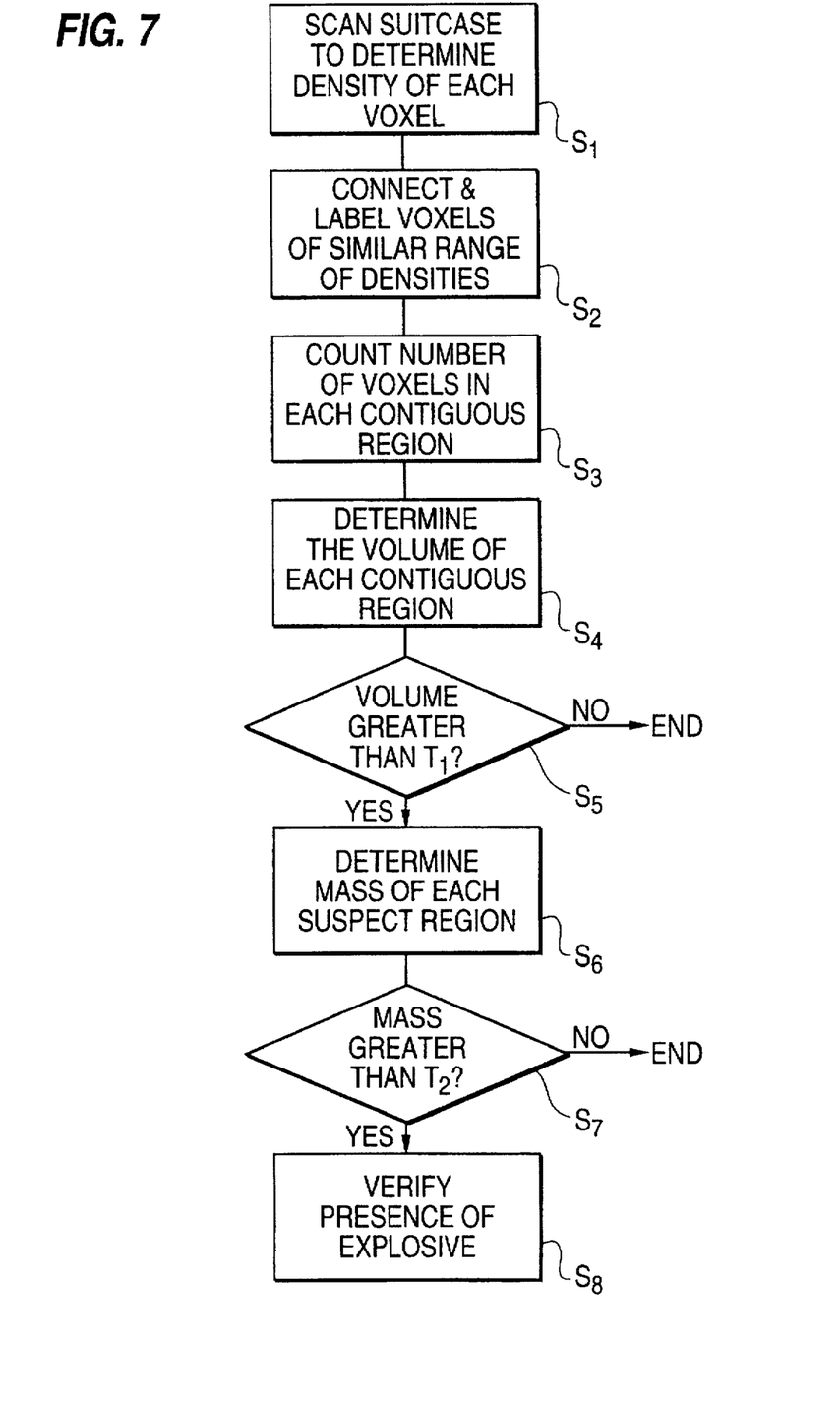
FIG. 7 is a flowchart for a technique to detect explosives in accordance with the invention.

A detailed example of the above-described technique will now be described with reference to FIG. 7. Most of the steps shown in FIG. 7 are performed in the contiguity identification module 210 and the object identification module 220 of processor 200. Depending on the specific application at hand, these modules can be implemented by software, hardware, or a combination of both.

It should be noted that the technique illustrated in FIG. 7 is only one example of an application of the principles of the invention. Those skilled in the field will appreciate that numerous modifications and variations of the FIG. 7 technique are possible.

The FIG. 7 example is based on the following a priori information:

(1) The explosive density is in the range of 1.2 to 1.8 gm/cc;
(2) The background density in the suitcase is approximately 0.2 gm/cc;
(3) The detection of small amounts of explosives, for example, 100 cc or 150 gm, is not desired; and
(4) Partial volume artifacts reduce density contrast in direct proportion to the lack of filling of a voxel.

Suitable modifications can be made to this a priori information based on the specifics of the detection problem at hand. In the FIG. 7 example, 0.3 to 1.8 gm/cc is selected as the density range of interest.

In step $S_1$ the suitcase is scanned to determine a linear attenuation coefficient for each voxel, which in turn represents the density of each voxel. Suitable techniques for scanning and density determination are described in the above-cited references concerning CT scanning. This density information is stored in a memory for processing in steps $S_2$ to $S_7$, which together identify potentially explosive regions in the CT image of the suitcase.

In step $S_2$, voxels having a similar range of densities, that is, similar densities between 0.3 and 1.8 gm/cc are connected and labelled as a contiguous region. In step $S_3$ the number of voxels in each contiguous region are counted. In step $S_4$ the volume of each contiguous, or connected and labeled, region is determined by multiplying the number of voxels for that region (from step $S_3$) by the voxel volume. Step $S_5$ determines, for each contiguous region, whether the volume of the contiguous region is greater than a threshold $T_1$, for example, 750 cc. Any region whose volume is greater than threshold $T_1$ is considered suspect and processing continues to step $S_6$.

In step $S_6$ the mass of each suspect contiguous region is determined by summing over the suspect contiguous region the product of each voxel density and voxel volume. Step $S_7$ determines whether the mass of each suspect contiguous region (from step $S_6$) is greater than threshold $T_2$, for example, 1000 gm. If the mass of a suspect contiguous region is greater than threshold T2, then the region is tentatively identified as explosive and processing proceeds to step $S_8$. Step $S_7$ could include activating an alarm. In step $S_8$ the presence, or absence, of an explosive is verified by an additional inspection method, for example, by pulsed fast neutron analysis or by opening the bag.

Because this new technique allows the use of large voxels instead of 2 mm voxels, the number of detector elements required is reduced. For example, if 1 cm voxels are used, the number of detector elements required is reduced to 100, the number of view angles is reduced to approximately 200, and the image size is reduced to 100×100. The input data set size, which is proportional to the number of detectors times the number of view angles, is therefore reduced by a factor of 25 (or more, because slice thickness can also be increased). The image reconstruction time, which is proportional to the number of view angles times the number of voxels in the image, is reduced by a factor of 125. These drastic reductions in data and computational load make practical and reliable CT systems for baggage inspection much simpler.

Although the invention has been described above with respect to certain specific applications and implementations of the invention, the scope of the invention is not limited to the specific applications and implementations described above. Various modifications, variations and applications within the spirit and scope of the invention will occur to those skilled in the field after receiving the above teachings. For example, the invention is not limited to the physical arrangement illustrated in FIGS. 3 and 4. Although the invention is particularly useful to detect sheet explosives in luggage, it is generally useful whenever an object of interest is smaller in one direction than the linear dimension of the voxels in the CT image, and can be used, for example, to detect and characterize delaminations in composite materials. Accordingly, the scope of the invention is defined by the following claims.

What is claimed is:

1. A method of detecting an explosive comprising the steps of:

(a) scanning a three-dimensional volume to determine the density of each of a plurality of voxels representing the three-dimensional volume;

(b) connecting and labeling voxels of the plurality of voxels which have similar densities;

(c) determining the volume of each contiguous region of voxels having similar densities;

(d) comparing the volume of each such contiguous region to a first threshold and identifying each such contiguous region which exceeds the first threshold as a suspect region;

(e) determining the mass of each suspect region; and (f) comparing the mass of each suspect region to a second threshold and identifying each suspect region which exceeds the second threshold as a region potentially containing an explosive.

2. A method as set forth in claim 1 further comprising the step of:

after step (f), further inspecting the three-dimensional volume to confirm the presence of an explosive.

3. A method as set forth in claim 2, wherein the further inspection includes manual inspection.

4. A method as set forth in claim 2, wherein the further inspection includes neutron interrogation.

5. An apparatus to detect an explosive, comprising:

(a) a scanner to scan a three-dimensional volume to determine the density of each of a plurality of voxels representing the three-dimensional volume; and (b) a processor which includes
 (1) a contiguity identification module to connect and label voxels of the plurality of voxels which have similar densities; and
 (2) an object identification module to
  (i) determine the volume of each contiguous region of voxels having similar densities;
  (ii) compare the volume of each such contiguous region to a first threshold and to identify each such contiguous region which exceeds the first threshold as a suspect region;
  (iii) determine the mass of each suspect region; and
  (iv) compare the mass of each suspect region to a second threshold and to identify each suspect region which exceeds the second threshold as a region potentially containing an explosive.

6. A method as set forth in claim 1, wherein in step (b) differences between a density of a given voxel and densities of voxels in planes above and below said given voxel, are employed to evaluate contiguity of said plurality of voxels.

* * * * *

EX PARTE REEXAMINATION CERTIFICATE (5617th)
United States Patent
Eberhard et al.

(10) Number: US 5,712,926 C1
(45) Certificate Issued: Nov. 28, 2006

(54) X-RAY COMPUTED TOMOGRAPHY (CT) SYSTEM FOR DETECTING THIN OBJECTS

(75) Inventors: Jeffrey Wayne Eberhard, Niskayuna, NY (US); Meng-Ling Hsiao, Niskayuna, NY (US)

(73) Assignee: L-3 Communications Security and Detection Systems, Inc., Woburn, MA (US)

Reexamination Request:
No. 90/007,648, Jul. 29, 2005

Reexamination Certificate for:
Patent No.: 5,712,926
Issued: Jan. 27, 1998
Appl. No.: 08/325,145
Filed: Oct. 20, 1994

(51) Int. Cl.
*G06K 9/46* (2006.01)

(52) U.S. Cl. .......................... 382/205; 378/57
(58) Field of Classification Search .......... 382/100, 382/205, 131, 154; 378/4, 20, 57, 62; 250/390.1, 250/390.4, 390.6
See application file for complete search history.

(56) References Cited

U.S. PATENT DOCUMENTS

| | | | |
|---|---|---|---|
| 4,991,224 A | 2/1991 | Takahashi | |
| 5,150,427 A | 9/1992 | Frazee | |
| 5,247,561 A | 9/1993 | Kotowski | |
| 5,442,672 A | * 8/1995 | Bjorkholm et al. | ............ 378/4 |

* cited by examiner

*Primary Examiner*—David E. Harvey (57) ABSTRACT

A technique to ascertain the presence or absence of an object in a three-dimensional volume, such as explosives in the side walls of luggage. The technique involves radiation scanning the three-dimensional volume to determine a property of each of a plurality of voxels representing the three-dimensional volume and to identify voxels having similar values of the property to identify a contiguous group of voxels having the similar values. Then, the contiguous group of voxels is identified as containing the object if a characteristic (such as mass and/or volume) of the contiguous group has a predetermined value.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–6 is confirmed.

* * * * *